(12) United States Patent
Serban et al.

(10) Patent No.: US 8,778,501 B2
(45) Date of Patent: Jul. 15, 2014

(54) FLUORESCENT POLYMERS FOR OXYGEN SENSING

(75) Inventors: Bogdan Catalin Serban, Bucharest (RO); Mihai N. Mihaila, Bucharest (RO); Octavian Buiu, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 217 days.

(21) Appl. No.: 13/308,730

(22) Filed: Dec. 1, 2011

(65) Prior Publication Data

US 2012/0141807 A1 Jun. 7, 2012

(30) Foreign Application Priority Data

Dec. 3, 2010 (EP) .................................. 10193630

(51) Int. Cl.
*G01N 21/64* (2006.01)
*G01N 31/22* (2006.01)
*C08G 73/02* (2006.01)

(52) U.S. Cl.
USPC ............ 428/426; 73/23.2; 524/299; 524/612; 528/422; 252/301.35; 422/83; 427/157; 428/913

(58) Field of Classification Search
USPC ......... 73/23.2; 252/301.35; 422/83; 427/157; 428/426, 913; 524/299, 612; 528/422
See application file for complete search history.

(56) References Cited

U.S. PATENT DOCUMENTS

2008/0264147 A1  10/2008  Serban et al.

FOREIGN PATENT DOCUMENTS

JP          04-351949 A    12/1992
WO    WO-2008/118740 A2    10/2008

OTHER PUBLICATIONS

Probing the Molecular Interactions at the Conducting Polyaniline Nanomaterial Surface via a Pyrene Fluorophore Shekhar D. Shinde and M. Jayakannan The Journal of Physical Chemistry C 2010 114 (36), 15491-15498 DOI: 10.1021/jp106022b.*
Amarnath, Chellachamy Anbalagan, et al. "Novel Electroluminescent Polymer Derived from Pyrene-Functionalized Polyaniline." Bull. Korean Chem. Soc 32.5 (2011): 1495. DOI: 10.5012/bkcs.2011.32.5.1495.*

"European Application Serial No. 10193630.0, Response filed Aug. 4, 2011 to Extended European Search Report mailed Apr. 4, 2011", 11 pgs.
"European Application Serial No. 101936300, Extended European Search Report mailed Apr. 4, 2011", 7 pgs.
Amao, Y., et al., "Fluorescence quenching oxygen sensor using an aluminum phthalocyanine-polystyrene film", *Analytica Chimica Acta*, 407(1-2). (Feb. 29, 2000), 41-44.
Fujiwara, Y., et al., "An oxygen sensor based on the fluorescence quenching of pyrene chemisorbed layer onto alumina plates", *Sensors and Actuators B*, 89, (2003), 187-191.
Serban, B., et al., "Calixarene-Doped Polyaniline for Applications in Sensing", *IEEE International Semiconductor Conference*, (2006), 257-260.
Wolfbeis, O. S., "Materials for fluorescence-based optical chemical sensors", *J. Mater. Chem.*, 15, (2005), 2657-2669.
Xu, W., et al., "Oxygen Sensors Based on Luminescence Quenching: Interactions of pyrene with the Polymer Supports"*Analytical Chemistry*, 67(18), (1995), 3172-3180.
Xu, W., et al., "Oxygen Sensors Based on Luminescence Quenching: Interactions of Metal Complexes with the Polymer Supports", *Analytical Chemistry*, 66(23), (1994), 4133-4141.

* cited by examiner

*Primary Examiner* — Callie Shosho
*Assistant Examiner* — John Freeman
(74) *Attorney, Agent, or Firm* — Schwegman, Lundberg & Woessner, P.A.

(57) ABSTRACT

A fluorescence based oxygen sensor can be prepared comprising a polyaniline polymer doped with one or more pyrene carboxylic acids. The polyaniline has the formula:

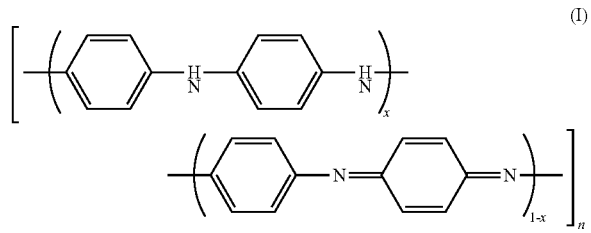

(I)

and the pyrene carboxylic acids have the formula:

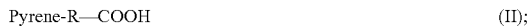

Pyrene-R—COOH    (II);

wherein R is an aliphatic linking group having 1 to 11 carbon atoms, n represents half the degree of polymerization, x is about 0.5, and (1−x) is about 0.5. The sensor can be coated onto a support. Upon excitation with an appropriate wavelength, the polyaniline/pyrene coating fluoresces. Upon exposure to oxygen the fluorescence rapidly decays.

13 Claims, No Drawings

FLUORESCENT POLYMERS FOR OXYGEN SENSING

PRIORITY CLAIM AND RELATED APPLICATION

This application claims the benefit of priority under 35 U.S.C. Section 119 to European Patent Application Serial No. 10193630.0, filed Dec. 3, 2010, which application is incorporated herein by reference in its entirety.

FIELD OF THE INVENTION

This invention relates to fluorescence polymers for oxygen sensors using a fluorescent polyaniline doped with a pyrene compound and to methods of preparing these sensors.

BACKGROUND

Determination of oxygen concentration is important in various fields such as automotive applications, medical devices, anesthesia monitors, and environmental monitoring. Recently, devices based on the fluorescence quenching of organic molecules have been developed to determine the concentration of oxygen. When exposed to light at an appropriate wavelength, the fluorescent substances absorb energy and are promoted from their ground state energy level (So) into an excited state energy level (S1). Fluorescent molecules are unstable in their excited states and can relax by different competing pathways.

Fluorescence based oxygen sensing elements work on the principle that relaxation of the S1 state can also occur through interaction with a second molecule through fluorescence quenching. Molecular oxygen ($O_2$) is an efficient quencher of fluorescence because of its unusual triplet ground state. Fluorophores used for oxygen sensing include: pyrene and its derivatives, quinoline, decacyclene and its derivatives, phenantrene, erythrosine B, and aluminum 2,9,16,23-tetraphenoxy-29H,31H-phthalocyaninehydroxide. These fluorophores are doped into a polymer matrix such as: silicones, polystyrene, and ethyl cellulose that are selectively permeable to oxygen and adhere to glass.

One difficulty with doping fluorescent molecules into a polymer is that the fluorescent molecule may have poor solubility and may crystallize or aggregate within the polymer matrix upon coating and drying.

It would be useful to provide an oxygen sensor that does not crystallize or aggregate within the polymer matrix upon coating and drying.

SUMMARY

A composition comprises a polyaniline (I) in the form of emeraldine base doped with one or more pyrene carboxylic acid compound (II) represented by Pyrene-R—COOH;

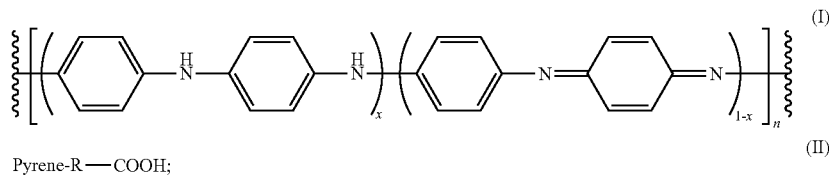

(I)

Pyrene-R—COOH;

(II)

wherein R is an aliphatic linking group having 1 to 11 carbon atoms, n represents half the degree of polymerization, x is about 0.5, and (1−x) is about 0.5.

A fluorescence oxygen sensor comprises a support having coated thereon: a polyaniline (I) in the form of emeraldine base doped with one or more pyrene carboxylic acid compound (II) represented by Pyrene-R—COOH;

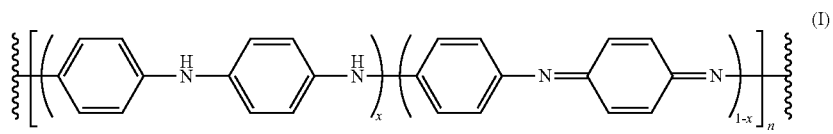

(I)

wherein R is an aliphatic linking group having 1 to 11 carbon atoms, n represents half the degree of polymerization, x is about 0.5, and (1−x) is about 0.5.

A method of preparing a fluorescence oxygen sensor comprises coating onto a support a solution of polyaniline (I) in the form of emeraldine base doped with one or more pyrene carboxylic acid compound (II) represented by Pyrene-R—COOH;

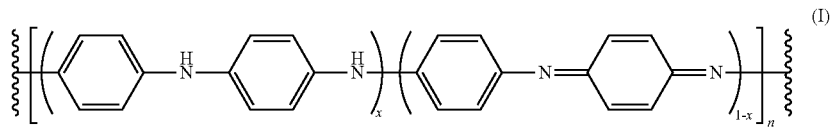

(I)

wherein R is an aliphatic linking group having 1 to 11 carbon atoms, n represents half the degree of polymerization, x is about 0.5, and (1−x) is about 0.5.

Other aspects, advantages, and benefits of the present invention are apparent from the detailed description, examples, and claims provided in this application.

DETAILED DESCRIPTION

To prevent aggregation and crystallization, the fluorescent pyrene molecule (a fluorophore) is immobilized by doping in a polyaniline matrix. Doping of a pyrene carboxylic acid compound into a polyaniline provides a fluorescence quenching oxygen sensor.

In one embodiment the pyrene fluorophore of the oxygen sensor comprises one or more pyrene aliphatic carboxylic acid compounds of formula (II) represented by Pyrene-R—COOH; wherein R is an aliphatic linking group having 1 to 11 carbon atoms.

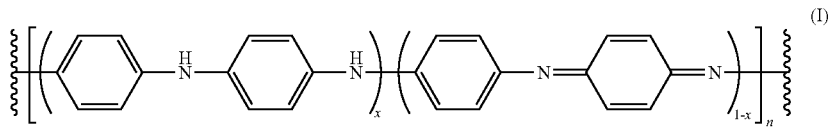
(I)

Polyaniline (I) can exist in one of three idealized oxidation states; leucoemeraldine—white/clear & colorless; emeraldine—green or blue, and pernigraniline—blue/violet. In compound (I), n equals half the degree of polymerization (DP). Leucoemeraldine with x is 1 and (1−x) is 0 is the fully reduced state. Pernigraniline is the fully oxidized state (x is 0 and (1−x) is 1) with imine links instead of amine links. The emeraldine form of polyaniline, often referred to as emeraldine base (EB) contains approximately equal amounts of amine and imine (i.e., x is about 0.5 and (1−x) is about 0.5). The emeraldine base is either neutral or doped, with the imine nitrogens protonated by an acid. It is regarded as the most useful form of polyaniline due to its high stability at room temperature and the fact that upon doping the emeraldine salt form of polyaniline is electrically conducting. Leucoemeraldine and pernigraniline are poor conductors, even when doped with an acid.

Representative pyrene carboxylic acid fluorophore compounds capable of being doped into the polyaniline include: pyrene butyric acid, pyrene decanoic acid, pyrene dodecanoic acid, and pyrene acetic acid. Mixtures of pyrene carboxylic acid fluorophore compounds may be used.

Exemplary pyrene carboxylic acid fluorophore compounds capable of being doped into the polyaniline include: 1-pyrene butyric acid (1), 1-pyrene decanoic acid (2), 1-pyrene dodecanoic acid (3), and 1-pyrene acetic acid (4). Mixtures of pyrene carboxylic acid fluorophore compounds may be used. These pyrene carboxylic acids are commercially available from Sigma-Aldrich (St. Louis, Mo.).

Structure (1) represents 1-pyrenebutyric acid.

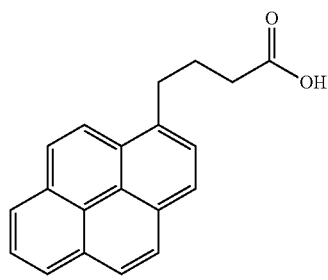
(1)

Structure (2) represents 1-pyrenedecanoic acid.

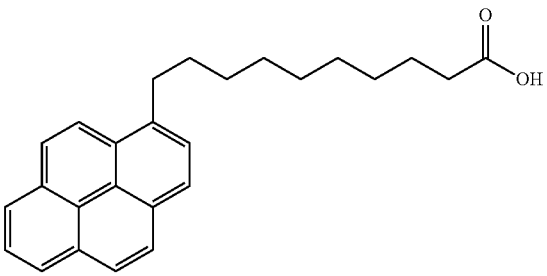
(2)

Structure (3) represents 1-pyrenedodecanoic acid.

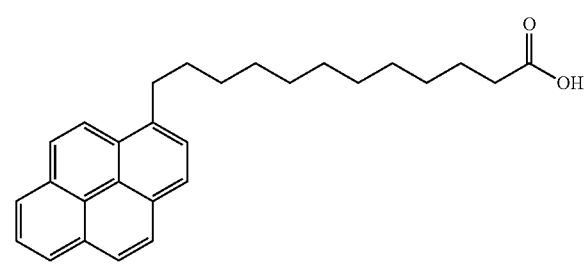
(3)

Structure (4) represents 1-pyrene acetic acid.

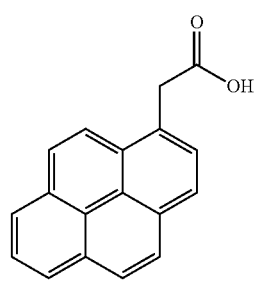
(4)

In formula (I) R is an alkylene group having from 1 to 11 carbon atoms. The alkylene group may be straight chain or branched. In one embodiment, R is a straight chain alkylene group —$(CH_2)_m$— having from 1 to 11 methylene groups. Particularly useful are —$(CH_2)_m$— groups wherein m is 1, 3, 9, and 11.

The amount of pyrene carboxylic acid and polyaniline can be determined experimentally by doping the polyaniline with various amounts of pyrene carboxylic acid until a strong fluorescence is obtained. In one embodiment, the weight ratio of pyrene carboxylic acid to polyaniline is from about 0.5:1 to about 4:1. A weight ratio of from about 2:1 to about 4:1 is also useful.

In one embodiment the oxygen sensor comprises a support. The support may be transparent, translucent, or opaque. The support may be rigid or flexible. Exemplary polymeric materials for making such supports include polyesters [such as poly(ethylene terephthalate) and poly(ethylene naphthalate)], cellulose acetate and other cellulose esters, polyvinyl acetal, polyolefins, polycarbonates, and polystyrenes. Preferred polymeric supports include polymers having good heat stability, such as polyesters and polycarbonates. Support materials may also be treated or annealed to reduce shrinkage and promote dimensional stability. Opaque supports can also be used, such metals and resin-coated papers that are stable to high temperatures. Rigid supports such as glass are also useful.

The fluorescence quenching quenching oxygen sensor can be prepared by coating the polyaniline/pyrene compounds of formula (I) onto a support using various coating procedures including spin coating, wire wound rod coating, dip coating, air knife coating, curtain coating, slide coating, or extrusion coating.

Preparation of Polyaniline

The preparation of polyaniline is shown below in Reaction Scheme (I). The acidification of polyaniline is shown below in Reaction Scheme (II).

Polyaniline (I) was prepared by chemical oxidation of aniline with ammonium peroxodisulphate. Aniline (23.3 g, 0.25 ml) was dissolved in 150 ml water, and then 20 ml of 37.5% hydrochloric acid was added to it. The mixture was stirred in an ice bath for one hour. Polymerization was started by addition of ammonium peroxodisulphate (57 g, 0.25 mol). After addition of ammonium peroxodisulphate, the solution was covered and placed in a refrigerator at 0° C. for six hours. After this, the mixture was diluted with water, and precipitate was filtered, washed with an excess of 0.5 M ammonium hydroxide, and then washed with deionized water. The resulting polyaniline, a dark powder, was dried at 60° C. for six hours to remove the solvent and water.

compound (II). Thereafter, the doped polyaniline is filtered and rinsed with water to remove the undissolved pyrene and form a homogeneous solution. The solution is coated onto a glass slide to form a film. The coated slide is stored for three days, after which the film is dried in vacuo at 50° C. for three hours. The film is then dried in a dessicator for three weeks.

Use of the Oxygen Sensor

The oxygen sensor may be incorporated in a miniature solid-state transducer that uses fluorescence to measure oxygen partial pressure. An LED excitation source and fluorescence detector are both integrated into the device. The device has a strong response to oxygen ($O_2$) but is insensitive to common atmospheric and medical gases. The polyaniline/pyrene is excited by the LED with an appropriate wavelength and fluoresces. Upon exposure to oxygen the fluorescence rapidly decays. The intensity and rate of decay of the fluorescence is measured by the detector.

References

Otto S. Wolfbeis, "Materials for fluorescence-based optical chemical Sensors", *J. Mater., Chem.*, 15, 2657-2669, (2005).

Wenying et al., "Oxygen sensors based on luminescence quenching: interactions of pyrene with the polymer supports", *Analytical Chem.*, 67, 3172-3180, (1995).

Y. Amao, K. Asai, I. Okura, "Fluorescence quenching oxygen sensor using an aluminum phthalocyanine-polystyrene film", *Analytica Chimica Acta*, 407, 41-44, (2000).

B. Serban, M. Bercu, S. Voicu, M. Mihaila, Gh. Nechifor, C. Cobianu., "Calixarenedoped polyaniline for applications in sensing", CAS 2006 Proceedings, pg. 257-260, IEEE catalog number: 06TH8867.

Scheme 1 - Preparation of Emeraldine Polyaniline

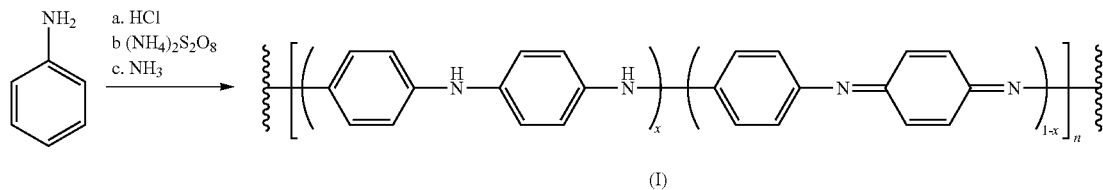

(I)

wherein x is about 0.5 and (1−x) is about 0.5 and n is the degree of polymerization.

B. Serban, Viorel V. Avramescu Cornel P. Cobianu, Ion Georgescu, N. Varachiu, "Design and deposition of sensing Scheme 2 - Acidification of Emeraldine Polyaniline

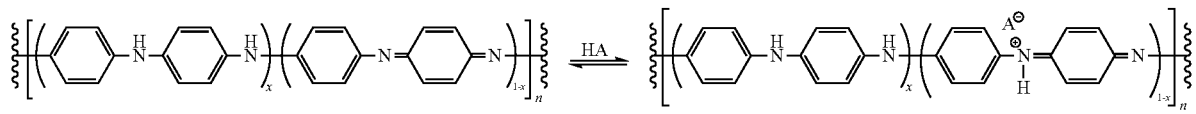

wherein x is about 0.5 and (1−x) is about 0.5, n is half the degree of polymerization, and $A^-$ is an anion of the acid, such as one or more pyrene carboxylic acid anions.

Preparation of Fluorescence Quenching Oxygen Sensors

Polyaniline polymer (0.5 g) as the free base is placed in 40 ml of dimethylformamide which contained 1 g of pyrene layers for surface acoustic chemical sensors based on supramolecular chemistry," WO 2008/118740, (Oct. 2, 2008).

B. Serban, Cobianu C, Bercu M., Varachiu N., Mihaila M., Bostan C., Voicu S., "Matrix nanocomposite containing aminocarbon nanotubes for carbon dioxide sensor detection,"

U.S. Patent Application Publication. No. 2008/0264147 A1, (Oct. 30, 2008).

The invention claimed is:

1. A composition comprising:

a polyaniline in the form of emeraldine base (I) doped with one or more pyrene carboxylic acid compounds (II) represented by Pyrene-R—COOH;

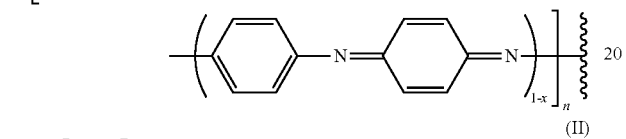

(I)

Pyrene-R—COOH;

(II)

wherein R is an aliphatic linking group having 1 to 11 carbon atoms, n represents half the degree of polymerization, x is about 0.5, and (1−x) is about 0.5.

2. The composition of claim 1, wherein the one or more pyrene carboxylic acid compounds (II) is selected from the group consisting of pyrene butyric acid, pyrene decanoic acid, pyrene dodecanoic acid, and pyrene acetic acid.

3. The composition of claim 1, wherein the one or more pyrene compounds (II) is selected from the group consisting of 1-pyrene butyric acid (1), 1-pyrene decanoic acid (2), 1-pyrene dodecanoic acid (3), and 1-pyrene acetic acid (4)

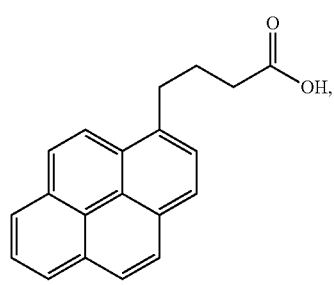

1-pyrene butyric acid
(1)

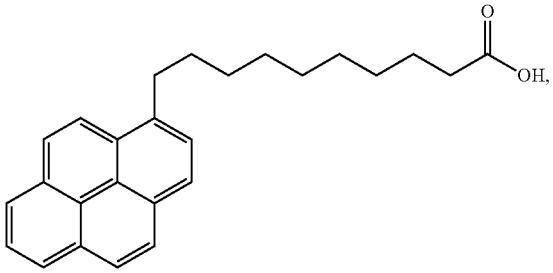

1-pyrene decanoic acid
(2)

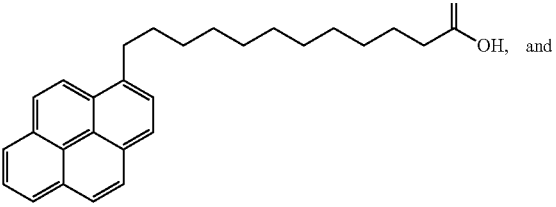

1-pyrene dodecanoic acid
(3)

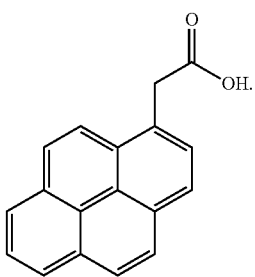

1-pyrene acetic acid
(4)

4. The composition of claim 1, coated onto a support.

5. The composition of claim 4, wherein the support is glass.

6. A fluorescence oxygen sensor comprising a support having coated thereon:

a composition comprising polyaniline in the form of emeraldine base (I) doped with one or more pyrene carboxylic acid compounds (II) represented by Pyrene-R—COOH;

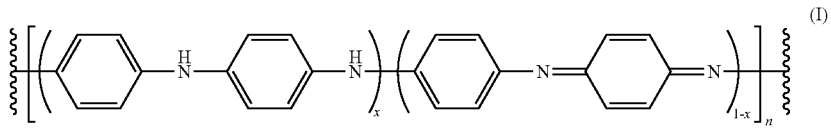

(I)

wherein R is an aliphatic linking group having 1 to 11 carbon atoms, and n represents half the degree of polymerization, x is about 0.5, and (1−x) is about 0.5.

7. The fluorescence oxygen sensor of claim 6, wherein the one or more pyrene carboxylic acid compounds (II) is selected from the group consisting of pyrene butyric acid, pyrene decanoic acid, pyrene dodecanoic acid, and pyrene acetic acid.

8. The fluorescence oxygen sensor of claim 6, wherein the one or more pyrene compound (II) is represented by 1-pyrene butyric acid (1), 1-pyrene decanoic acid (2), 1-pyrene dodecanoic acid (3), and 1-pyrene acetic acid (4)

(1)

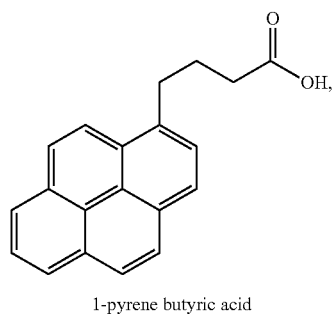

1-pyrene butyric acid

-continued (2)

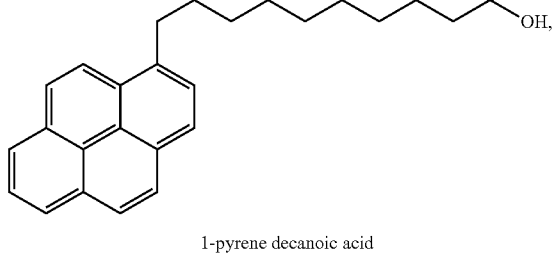

1-pyrene decanoic acid (3)

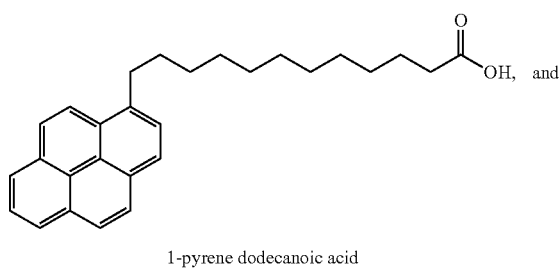

1-pyrene dodecanoic acid

-continued (4)

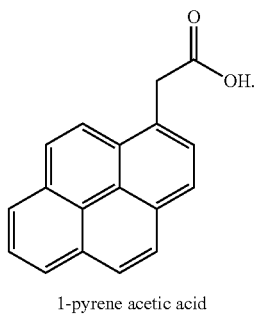

1-pyrene acetic acid

9. The fluorescence oxygen sensor of claim 6, further comprising a LED excitation source and a fluorescence detector.

10. A method of preparing a fluorescence oxygen sensor of claim 6, comprising coating onto a support a solution of a composition comprising polyaniline in the form of emeraldine base (I) doped with one or more pyrene carboxylic acid compounds (II) represented by Pyrene-R—COOH;

(I)

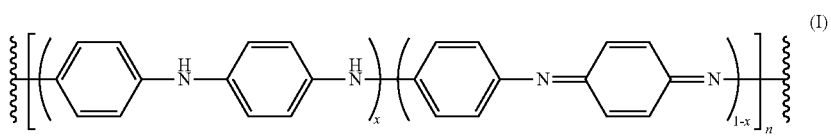

wherein R is an aliphatic linking group having 1 to 11 carbon atoms and n represents half the degree of polymerization, x is about 0.5, and (1−x) is about 0.5.

11. The method of claim 10, wherein R is —$(CH_2)_m$— and m is 1 to 11.

12. The method of claim 10, wherein Pyrene-R—COOH is represented by one or more of:

(1)

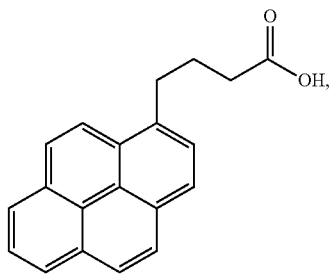

(2)

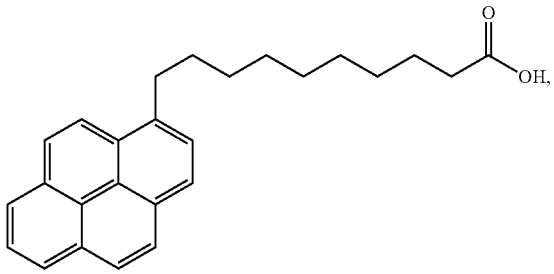

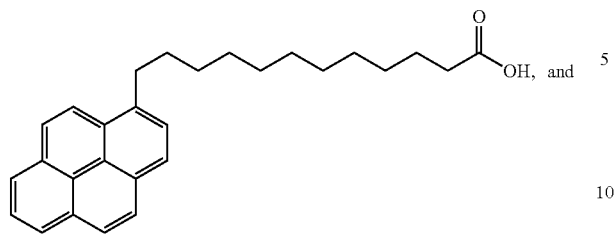
13. The method of claim 10, wherein the support is glass.
* * * * *